United States Patent [19]

Enjo et al.

[11] Patent Number: 4,623,475
[45] Date of Patent: Nov. 18, 1986

[54] FLUOROCHLOROHYDROCARBON COMPOSITIONS

[75] Inventors: Naonori Enjo, Suita; Yuhkow Harada, Ibaraki, both of Japan

[73] Assignee: Daikin Kogyo Co., Ltd., Japan

[21] Appl. No.: 655,527

[22] Filed: Sep. 28, 1984

[30] Foreign Application Priority Data

Sep. 30, 1983 [JP] Japan ................................ 58-183870

[51] Int. Cl.$^4$ ............................................... C09K 5/04
[52] U.S. Cl. ........................................ 252/68; 252/67
[58] Field of Search ................................... 252/67, 68

[56] References Cited

U.S. PATENT DOCUMENTS

| | | | |
|---|---|---|---|
| 2,550,113 | 4/1951 | Flowers | 252/68 |
| 3,944,494 | 3/1976 | Mahler | 252/67 |
| 4,068,706 | 1/1978 | Mahler | 252/68 |
| 4,454,052 | 6/1984 | Shoji et al. | 252/68 |

FOREIGN PATENT DOCUMENTS 58-208375 12/1983 Japan ................................ 252/68

*Primary Examiner*—Paul Lieberman
*Assistant Examiner*—Robert A. Wax
*Attorney, Agent, or Firm*—Larson and Taylor

[57] ABSTRACT

The invention provides fluorochlorohydrocarbon compositions containing as a stabilizer a boron compound or a boron compound and an ester of phosphorous acid. The compositions are for use as a heating medium, a foaming agent for the preparation of foamed products of plastics or the like.

5 Claims, No Drawings

FLUOROCHLOROHYDROCARBON COMPOSITIONS

This invention relates to fluorochlorohydrocarbon compositions and more particularly to fluorochlorohydrocarbon compositions containing as a stabilizer a boron compound or a boron compound and an ester of phosphorous acid. The compositions of the present invention are useful as a heating medium such as a refrigerant and a working fluid for heat pipes, a foaming agent for use in the preparation of foamed plastics bodies or the like.

Fluorochlorohydrocarbon (hereinafter referred to as "Flon") is extensively used as a refrigerant for refrigerators. A refrigerant is heated to a high temperature by a compressor in a refrigeration cycle. Flon, which is a stable compound, does not decompose under normal conditions in a refrigeration cycle, but may decompose at a high condensation temperature or a low volatilization temperature which greatly increases the temperature in the compressor.

Power generation which utilizes a Rankine cycle using Flon has been put to practical use in recent years. Flon used in the refrigerator or the system involving a Rankine cycle is brought into contact with a lubricating oil and metals. Further, Flon comes into contact with metals when working in a heat transfer device in which Flon is charged in a pipe. Also metals coexist with Flon used as a foaming agent in preparing foamed bodies of plastics such as polyurethane, polystyrene, polyethylene, polypropylene, polyvinyl chloride, ethylene-vinyl acetate copolymer or the like. In such case, the metals act to render Flon more decomposable. Flon tends to decompose on contact with a lubricating oil and metals to a greater extent than with a lubricating oil alone.

In the foregoing situation where Flon and lubricating oils are decomposed, the thermodynamic characteristic of Flon and the lubricity of the lubricating oil are impaired, and the refrigerator and the system utilizing a Rankine cycle are given a lower capability. Further the decomposition of Flon produces halogen which corrodes metals, and the corrosion of the metal forms hydrogen which deteriorates the function of the heat exchanging device in a refrigerator or the like. The same problems are encountered with the aforesaid heat transfer devices.

With the recent development of highly efficient apparatus and equipment using Flon, a variety of methods for preventing the decomposition of Flon and those for removing the decomposition products have been proposed to overcome the problem of the increase in the temperature involved in use of Flon. The proposed methods for preventing the decomposition of Flon include, for example, adding as a stabilizer furan (Japanese Examined Patent Publication No. 22374/1965), nitrous oxide (Japanese Unexamined Patent Publication No. 49685/1973), an ester of phosphorous acid (Japanese Unexamined Patent Publication No. 48277/1980), and dialkylbenzoerythritol diphosphite (Japanese Unexamined Patent Publication No. 70082/1981). The proposed methods for removing the decomposition products include adsorption by an adsorbent. However, the proposed methods remain to be improved to achieve the high degree of ability currently required. More specifically, the additives used in the proposed methods fail to prevent the decomposition of Flon to the desired extent or are not usable in heat transfer devices (such as heat pipes) or as a foaming agent for the production of foamed plastics bodies.

An object of the present invention is to provide Flon compositions which are less susceptible to decomposition at high temperatures.

Another object of the invention is to provide Flon compositions which can exhibit stability when brought into contact with metals and/or lubricating oils.

A further object of the invention is to provide Flon compositions which are suitable for use as a heating medium in a heat exchanging device such as a refrigerator and in a heat transfer device such as a heat pipe.

An additional object of the invention is to provide Flon compositions which are useful as a foaming agent in the preparation of foamed plastics bodies.

Other objects and features of the present invention will become apparent from the following description.

The present invention provides fluorochlorohydrocarbon compositions comprising a fluorochlorohydrocarbon and a boron compound.

The present invention further provides fluorochlorohydrocarbon compositions comprising a fluorochlorohydrocarbon, a boron compound and an ester of phosphorous acid.

To overcome the foregoing problems of conventional Flon compositions, we conducted extensive research in an attempt to obtain Flon compositions having higher stability and improved properties and found that when using a specific type of boron compound as a stabilizer, the decomposition of Flon is effectively inhibited. We further discovered that Flon containing a combination of a specific type of boron compound and an ester of phosphorous acid as a stabilizer has higher stability. Based on these findings, the present invention has been accomplished.

The term fluorochlorohydrocarbon used throughout the specification and the appended claims refer to compounds in which at least one hydrogen atom of the saturated aliphatic hydrocarbons is substituted with fluorine and at least one hydrogen atom thereof with chlorine and which have 1 to 6 carbon atoms, preferably 1 or 2 carbon atoms. Preferred examples of fluorochlorohydrocarbons are chlorodifluoromethane, dichlorodifluoromethane, trichlorofluoromethane, chloropentafluoromethane, dichlolotetrafluoromethane, trichlorotrifluoromethane and the like to which, however, the fluorochlorohydrocarbons usable in the present invention are not limited.

The boron compound used in the present invention is at least one compound selected from the group consisting of boron oxide, boric acid, alkali metal salt of boric acid, metaboric acid, alkali metal salt of metaboric acid, phenyl ester and alkyl ester of boric acid, phenylboronic acid, phenyl ester and alkyl ester of phenylboronic acid, diphenylborinic acid, and phenyl ester and alkyl ester of diphenylborinic acid. Preferred alkyl esters of the acids are those with alkyl having 1 to 5 carbon atoms. Usable dialkyl esters and trialkyl esters of the acids include those in which alkyl groups are different or the same. Given below are preferred examples of boron compounds according to the present invention.

Boric acid type: boron oxide, boric acid, borax, potassium tetraborate, sodium metaborate; monophenyl borate, diphenyl borate, triphenyl borate, monoalkyl borate, dialkyl borate, trialkyl borate and the like having alkyl such as methyl, ethyl, n-propyl or isopropyl; etc.

Phenylboronic acid type: phenylboronic acid, monophenylmonophenyl boronate, diphenylmonophenyl boronate; monoalkylphenyl boronate, dialkylphenyl boronate and the like having alkyl such as methyl, ethyl, n-propyl or isopropyl; etc.

Diphenylborinic acid type: diphenylborinic acid, monophenyldiphenyl borinate; monoalkyldiphenyl borinate and the like having alkyl such as methyl, ethyl, n-propyl or isopropyl; etc.

The amount of the boron compound contained in the present composition is not particularly limited, and generally ranges from about 0.01 to about 5%, preferably about 0.1 to about 5%, by weight of the fluorochlorohydrocarbon. If less than 0.01% by weight of the boron compound is present, the composition can not exhibit the desired stability. With over 5% by weight of the compound, the composition can not produce correspondingly more improved results.

The ester of phosphorous acid used in the present invention is at least one compound selected from the group consisting of alkyl ester and aryl ester of phosphorous acid and alkylpentaerythritol phosphite. Of these esters, it is preferred to use dialkyl phosphite having 2 to 30 carbon atoms, diphenyl phosphite having 2 to 30 carbon atoms and dialkylpentaerythritol phosphite having 7 to 45 carbon atoms. Useful dialkyl esters include those in which alkyl groups are the same or different. Suitable examples of esters of phosphorous acids are as follows.

Alkyl ester: dimethyl phosphite, diethyl phosphite, di-n-propyl phosphite, diisopropyl phosphite, dibutyl phosphite, dilauryl phosphite, etc.

Aryl ester: diphenyl phosphite, etc.

Alkylpentaerythritol phosphite: diethylpentaerythritol diphosphite, dioctylpentaerythritol diphosphite, didecylpentaerythritol diphosphite, distearylpentaerythritol diphosphite, etc.

In the present composition containing a boron compound and an ester of phosphorous acid in combination, it is preferred to use 5% or more by weight of the boron compound and more preferred to employ 5 to 95% by weight of the boron compound and 95 to 5% by weight of the ester of phosphoric acid, based on the whole weight of the two components.

The total amount of the boron compound and ester of phosphorous acid is not particularly limited and ranges usually from about 0.01 to about 5% by weight, preferably about 0.1 to about 5% by weight, based on the weight of Flon. Below 0.01% by weight or above 5% by weight, the desired results can not be achieved to a sufficient extent.

The boron compound or the boron compound and ester of phosphorous acid are added directly to Flon or dissolved in a suitable solvent to provide a solution which is added to Flon. Suitable solvents are those which are capable of dissolving the boron compound and the ester of phosphorous acid and also dissolving itself in Flon without reaction with Flon and which is thermally stable. Specific examples of such solvents are dioxane, methyl acrylate, tertiary butanol and the like.

The Flon compositions of the present invention can achieve the following results.

(1) The Flon compositions of the present invention are more stable at high temperatures than Flon compositions containing a conventional stabilizer. For example, a composition containing trichlorofluoromethane (Flon-11) as a working fluid can be used at a temperature higher by 40° C. by incorporating a boron compound singly or in conjunction with an ester of phosphorous acid.

(2) The present Flon compositions are less susceptible to decomposition in contact with a lubricationg oil and/or metals than conventional Flon compositions.

(3) The present Flon compositions are less corrosive to metal portions of apparatus and devices than conventional Flon compositions.

(4) The present Flon compositions are outstanding as a foaming agent for use in producing foamed bodies of plastics such as polyurethane, polystyrene, polyethylene, polypropylene, polyvinyl chloride, ethylene-vinyl acetate copolymer, etc.

Examples and comparison examples are given below to clarify the features of the present invention.

EXAMPLES 1 TO 4 AND COMPARISON EXAMPLES 1 TO 5

Into a heat-resistant glass tube measuring 6 mm in inside diameter, 10 mm in outer diameter and 250 mm in length were placed a composition comprising 2 g of trichlorofluoromethane and each of additives as shown below in Table 1 and then 0.02 g of a lubricating oil (JIS turbine oil No. 1) and a steel piece (JIS SS41, 2 mm×5 mm×50 mm). The glass tube was sealed and heated at 150° C. for 100 hours. Thereafter the appearance of the composition and the steel piece was observed and the amount of the chlorine compound present in the composition and also deposited on the steel piece was measured by ion-exchange chromatography. Table 1 below shows the results.

The appearance of the steel piece and the composition was evaluated by the following criteria.

(i) Appearance of steel piece
A: No change
B: Disclored to pale brown
(ii) Appearance of composition
A: No change
B: Colored yellow
C: Colored brown

TABLE 1

|  | Additive | Additive conc. (%) | Cl conc. (ppm) after heating | Metal appearance | Composition appearance |
|---|---|---|---|---|---|
| Com. Ex. 1 | None | 0 | 1500 | B | C |
| Com. Ex. 2 | Dimethyl phosphite | 0.3 | 37 | A | A |
| Com. Ex. 3 | Furan | 0.3 | 300 | B | B |
| Com. Ex. 4 | Diethylpentaerythritol diphosphite | 0.3 | 35 | A | A |
| Com. Ex. 5 | Triphenyl phosphite | 0.5 | 25 | A | A |
| Ex. 1 | Triphenyl borate | 0.1 | 50 | A | A |
| Ex. 2 | Triphenyl borate | 0.25 | 15 | A | A |
| Ex. 3 | Triphenyl | 0.5 | 8 | A | A |

TABLE 1-continued

| | Additive | Additive conc. (%) | Cl conc. (ppm) after heating | Metal appearance | Composition appearance |
|---|---|---|---|---|---|
| Ex. 4 | borate Methyldiphenyl borate | 0.5 | 10 | A | A |

Table 1 reveals that, of the boron compounds usable in the present invention, triphenyl borate in a low concentration can inhibit the decomposition of Flon more effectively than conventional stabilizers such as an ester of phosphorous acid.

EXAMPLES 5 TO 7

The general procedures of Examples 1 to 4 were repeated except that the additives listed below in Table 2 were dissolved in solvents shown below in Table 2. Table 2 below indicates the results.

TABLE 2

| | Additive (solvent) | Additive conc. (%) | Cl conc. (ppm) after heating | Metal appearance | Composition appearance |
|---|---|---|---|---|---|
| Ex. 5 | Triphenyl borate | 0.1 | 42 | A | A |
| | (Dioxane) | 0.1 | | | |
| Ex. 6 | Triphenyl borate | 0.1 | 13 | A | A |
| | (Methyl acrylate) | 0.1 | | | |
| Ex. 7 | Triphenyl borate | 0.1 | 40 | A | A |
| | (t-Butyl alcohol) | 0.1 | | | |

It is clear from the comparison of the results in Tables 1 and 2 that when incorporating into a fluorochlorohydrocarbon a solution of a boron compound in a solvent, there results more improved effect than when singly using a boron compound.

EXAMPLES 8 TO 12 AND COMPARISON EXAMPLES 6 TO 10

Into the same glass tube as used in Examples 1 to 4 were placed 2 g of trichlorofluoroethane, a copper piece (2 mm × 5 mm × 50 mm), and each of boron compounds and each of solvents shown below in Table 3. The glass tube was sealed and heated at 200° C. for 10 days. Table 3 below shows the evaluation of the appearance of the copper piece and trichlorofluoroethane and the concentrations of the chlorine compound contained in the trichlorofluoroethane and deposited on the metal surface.

TABLE 3

| | Additive (solvent) | Additive conc. (%) | Cl conc. (ppm) after heating | Metal appearance | Composition appearance |
|---|---|---|---|---|---|
| Com. Ex. 6 | None | 0 | 260 | B | B |
| Com. Ex. 7 | Dimethyl phosphite | 0.3 | 250 | B | B |
| Com. Ex. 8 | Furan | 0.3 | 630 | C | C |
| Com. Ex. 9 | Diethylpentaerythritol diphosphite | 0.3 | 250 | B | C |
| Com. Ex. 10 | Triphenyl phosphite | 0.3 | 140 | B | A |
| Ex. 8 | Triphenyl borate | 0.1 | 65 | B | B |
| Ex. 9 | Triphenyl borate | 0.25 | 30 | A | A |
| Ex. 10 | Triphenyl borate | 0.5 | 26 | A | A |
| Ex. 11 | Triphenyl borate (Dioxane) | 0.25 0.25 | 8 | A | A |
| Ex. 12 | Triphenyl borate (Methyl acrylate) | 0.25 0.25 | 7 | A | A |

Table 3 shows that when using, in the absence of a lubricating oil, a boron compound which is not dissolved in a solvent, the decomposition of Flon is effectively inhibited.

The same results as above were obtained when steel was used as a metal.

EXAMPLES 13 TO 22 AND COMPARISON

EXAMPLES 11 TO 15

Into a heat-resistant glass tube measuring 6 mm in inside diameter, 10 mm in outer diameter and 250 mm in length were placed a composition comprising 2 g of trichlorofluoromethane and each of additives shown below in Table 4, and then 0.02 g of a lubricating oil (JIS turbine oil No. 1) and a steel piece (JIS SS41, 2 mm × 5 mm × 50 mm). The glass tube was sealed and heated at 130° C. over specified periods of time. Thereafter the appearance of the composition was observed and the concentration of the chlorine compound present in the composition and deposited on the steel piece was measured with the results as shown below in Table 4.

TABLE 4

| | Additive | Additive conc. (%) | Cl conc. (ppm) after heating 480 hours | Cl conc. (ppm) after heating 1080 hours | Composition appearance 480 hours | Composition appearance 1080 hours |
|---|---|---|---|---|---|---|
| Com. Ex. 11 | None | 0 | 1100 | 3800 | B | C |
| Com. Ex. 12 | Dimethyl phosphite | 0.2 | 26 | 1400 | A | B |
| Com. Ex. 13 | Dimethyl phosphite | 0.02 | 250 | 3000 | B | C |
| Com. Ex. 14 | Diphenyl phosphite | 0.2 | 21 | 1300 | A | B |
| Com. Ex. 15 | Diethylpentaerythritol diphosphite | 0.2 | 20 | 1000 | A | B |
| Ex. 13 | Triphenyl borate | 0.2 | 13 | 420 | A | B |
| Ex. 14 | Triphenyl borate | 0.02 | 110 | 980 | A | B |
| Ex. 15 | Triphenyl borate | 0.1 | 8 | 30 | A | A |
| | Dimethyl phosphite | 0.1 | | | | |
| Ex. 16 | Triethyl borate | 0.02 | 10 | 90 | A | A |
| | Dimethyl phosphite | 0.18 | | | | |
| Ex. 17 | Triphenyl borate | 0.01 | 12 | 370 | A | A |
| | Dimethyl phosphite | 0.01 | | | | |
| Ex. 18 | Triphenyl borate | 0.1 | 7 | 28 | A | A |
| | Diphenyl phosphite | 0.1 | | | | |
| Ex. 19 | Triphenyl borate | 0.1 | 7 | 28 | A | A |
| | Diethylpentaerythritol diphosphite | 0.1 | | | | |
| Ex. 20 | Methyldiphenyl borinate | 0.1 | 10 | 50 | A | A |
| | Diphenyl phosphite | 0.1 | | | | |
| Ex. 21 | Triethyl borate | 0.1 | 12 | 110 | A | A |
| | Dilauryl phosphite | 0.1 | | | | |
| Ex. 22 | Boric acid | 0.05 | 13 | 330 | A | A |
| | Dimethyl phosphite | 0.15 | | | | |

Table 4 demonstrates that the conjoint use of triphenyl borate and an ester of phosphorous acid results in a pronouncedly enhanced effect in preventing the decomposition of Flon, as compared with the use of conventional stabilizers.

EXAMPLES 23 AND 24 AND COMPARISON EXAMPLES 16 AND 17

Heating tests were conducted by repeating the general procedures of Comparison Examples 11 and 12 and Examples 13 and 15 with the exception of using 1 g of each of trichlorofluoromethane and the lubricating oil.

Table 5 below shows the results obtained after 480 hours of heating.

TABLE 5

| | Additive | Additive conc. (%) | Cl conc. (ppm) after heating | Composition appearance after heating |
|---|---|---|---|---|
| Com. Ex. 16 | None | 0 | 3000 | C |
| Com. Ex. 17 | Dimethyl phosphite | 0.2 | 35 | A |
| Ex. 23 | Triphenyl borate | 0.2 | 21 | A |
| Ex. 24 | Triphenyl borate | 0.1 | 15 | A |
| | Dimethyl phosphite | 0.1 | | |

EXAMPLES 25 AND 26 AND COMPARISON EXAMPLES 18 AND 19

Heating tests were carried out by repeating the general procedures of Comparison Examples 11 and 12 and Examples 13 and 15 with the exception of using 1 g of each of trichlorofluoromethane and the lubricating oil and three kinds of metal pieces (the same steel piece as used in Examples 1 to 4, a copper piece measuring 2 mm×5 mm×50 mm and an aluminum piece measuring 2 mm×5 mm×50 mm). Table 6 indicates the results obtained after heating for specified periods of time.

TABLE 6

| | Additive | Additive conc. (%) | Cl conc. (ppm) after heating | | Composition appearance | |
|---|---|---|---|---|---|---|
| | | | 480 hours | 1080 hours | 480 hours | 1080 hours |
| Com. Ex. 18 | None | 0 | 6000 | >10000 | C | C |
| Com. Ex. 19 | Dimethyl phosphite | 0.2 | 460 | 5400 | A | B |
| Ex. 25 | Triphenyl borate | 0.2 | 300 | 670 | A | A |
| Ex. 26 | Triphenyl borate | 0.1 | 180 | 320 | A | A |
| | Dimethyl phosphite | 0.1 | | | | |

We claim:

1. A fluorochlorohydrocarbon composition comprising:
   (i) a fluorochlorohydrocarbon,
   (ii) a boron compound selected from the group consisting of boron oxide, boric acid, alkali metal salt of boric acid, metaboric acid, alkali metal salt of metaboric acid, phenyl ester and alkyl ester of boric acid, phenylboronic acid, alkyl ester of phenylboronic acid, diphenylboronic acid, and alkyl ester of diphenylboronic acid, and
   (iii) an ester of phosphoric acid selected from the group consisting of dialkyl phosphite having 2 to 30 carbon atoms, diphenyl phosphite having 2 to 30 carbon atoms and dialkylpentaerythritol diphosphite having 7 to 45 carbon atoms;
   the amount of the boron compound being at least 5% by weight based on the total weight of the boron compound and the ester of phosphorous acid and the total amount of these two compounds being about 0.01 to about 5% by weight based on the weight of the fluorochlorohydrocarbon.

2. A fluorochlorohydrocarbon composition as defined in claim 1 in which fluorochlorohydrocarbon has 1 to 6 carbon atoms.

3. A fluorochlorohydrocarbon composition as defined in claim 2 in which fluorochlorohydrocarbon has 1 to 2 carbon atoms.

4. A fluorochlorohydrocarbon composition as defined in claim 1 in which the weight ratio of the boron compound to the ester of phosphorous acid ranges from 5:95 to 95:5.

5. A fluorochlorohydrocarbon composition as defined in claim 1 in which the total amount of the boron compound and the ester of phosphorous acid is about 0.1 to about 5% by weight based on the weight of the fluorochlorohydrocarbon.

* * * * *